United States Patent
DeSilets et al.

(10) Patent No.: US 7,254,438 B2
(45) Date of Patent: *Aug. 7, 2007

(54) MULTIMODALITY MEDICAL IMAGING SYSTEM AND METHOD WITH INTERVENING PATIENT ACCESS AREA

(75) Inventors: Mark DeSilets, San Jose, CA (US); Jacco Eerden, Eindhoven (NL); Horace H. Hines, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 157 days.

This patent is subject to a terminal disclaimer.

(21) Appl. No.: 10/027,843

(22) Filed: Oct. 19, 2001

(65) Prior Publication Data

US 2003/0078488 A1  Apr. 24, 2003

(51) Int. Cl.
 *A61B 5/05* (2006.01)
(52) U.S. Cl. ............ 600/427; 600/411; 600/436; 378/4; 378/21; 250/363.02; 250/363.03; 250/363.04
(58) Field of Classification Search ........ 600/410–415, 600/425, 427, 407, 436; 601/2–4; 378/62–65, 378/4, 21, 209; 324/307, 309; 250/363.03, 250/363.04, 363.05, 363.01, 363.02; 5/600–601, 5/606, 84.1
See application file for complete search history.

(56) References Cited

U.S. PATENT DOCUMENTS

| | | |
|---|---|---|
| 5,178,146 A | 1/1993 | Giese |
| 5,349,956 A | 9/1994 | Bonutti |
| 5,525,905 A | 6/1996 | Mohapatra et al. |
| 5,562,094 A | 10/1996 | Bonutti |
| 5,713,357 A | 2/1998 | Tuithof et al. |
| 5,851,182 A | 12/1998 | Sahadevan |
| 6,003,174 A * | 12/1999 | Kantrowitz et al. ........... 5/601 |
| 6,205,347 B1 | 3/2001 | Morgan et al. |
| 6,302,579 B1 | 10/2001 | Meyer et al. |
| 6,490,476 B1 * | 12/2002 | Townsend et al. .......... 600/427 |
| 6,591,127 B1 * | 7/2003 | McKinnon .................. 600/411 |
| 6,603,991 B1 | 8/2003 | Karmalawy et al. |
| 6,637,453 B2 * | 10/2003 | Robinson .................... 137/312 |
| 6,754,519 B1 * | 6/2004 | Hefetz et al. ............... 600/407 |
| 6,754,520 B2 * | 6/2004 | DeSilets et al. ............ 600/415 |
| 6,775,405 B1 * | 8/2004 | Zhu ........................... 382/154 |
| 6,961,606 B2 * | 11/2005 | DeSilets et al. ............ 600/415 |
| 7,071,692 B2 * | 7/2006 | Branch et al. .............. 324/318 |
| 2002/0032927 A1 * | 3/2002 | Dinkler ........................ 5/601 |

FOREIGN PATENT DOCUMENTS

WO   WO 00/75691 A1   12/2000

* cited by examiner

*Primary Examiner*—Eleni Mantis Mercader
*Assistant Examiner*—Amanda L. Lauritzen

(57) ABSTRACT

The invention comprises a system and method for creating medical images of a subject patient using a plurality of imaging devices, such as tomographic imaging scanners. The system comprises a plurality of imaging devices, each having a bore through which a patient is translated during scanning. The bores of each device are substantially aligned axially with respect to each other. An open area is formed between the imaging devices along the path of the patient, through which a caregiver can attain line-of-sight visual contact with or other access to the patient. During a scanning operation, the scanned portion of a patient is transported through the bore of the first device, past the opening between the devices and into the bore of the second device.

29 Claims, 3 Drawing Sheets

MULTIMODALITY MEDICAL IMAGING SYSTEM AND METHOD WITH INTERVENING PATIENT ACCESS AREA

TECHNICAL FIELD

The invention relates to multimodality medical imaging systems for viewing anatomical structures and functions of a patient, such as combined x-ray Computed Tomography (CT) and Positron Emission Tomography (PET) scanners and, more particularly, to facilitating patient handling and access, expediting interventional applications and enhancing patient comfort during the multimodality medical imaging process.

BACKGROUND OF THE INVENTION

Tomographic imaging devices or cameras are frequently used to assist in the diagnosis and treatment of a variety of anatomical structures and physiologic functions within the body of a subject patient, while minimizing the need for invasive procedures. Such devices typically utilize scanners that obtain data or information about such structures and functions from the patient at specified, discrete locations along the length of a patient. Using this information, the camera produces a series of images, each depicting a cross-section of the body of the patient, in a plane generally perpendicular to the length of the patient, and at specified points along the length of the patient. Combined, successive images or a substantially continuous spiral image taken along the length of a patient can yield a relatively three-dimensional view of internal organs and tissues, or at least provide a cross-sectional view of bodily structures or functions at various places on the patient. Tomographic cameras are most frequently used to view and treat organs and other tissues within the head, torso and trunk of a patient and, in particular, diagnose and treat such ailments as heart disease, arteriosclerosis, cancer, and the like.

Tomographic imaging cameras are often identified by the "mode" or "modality" of radiation used by their scanners to obtain patient data. Well-known scanner modalities include the X-ray Computed Tomography (CT), Magnetic Resonance Imaging (MRI), Ultra-sound (ULT), Single Photon Emission Computed Tomography (SPECT) and Positron Emission Tomography (PET) scanners. Camera systems which combine two or more different scanners to obtain a greater variety of imaging information from a patient are referred to as "multimodality imaging systems." Conversely, tomographic cameras utilizing the same mode to collect imaging information are referred to as having the same modality.

A tomographic camera utilizes a scanner having an array of radiation detectors forming a ring or bore that surrounds a patient. The scanner gathers information along a plane defined by the detector ring, which intersects the patient substantially perpendicularly to the length of the patient. Other processors and instruments coupled to the scanner form the topographic image, based on information received from the scanner. To obtain information at successive points along the head, torso and trunk of a patient, the patient is supported horizontally on a patient table that translates or moves the patient horizontally through the bore of a tomographic camera.

It is often desirable to utilize two or more adjacent tomographic scanners of different modalities, in multimodality systems, to obtain a variety of imaging information from a single traverse of a patient through multiple scanner bores. This is highly desirable as a means of increasing efficiency (by completing two or more scans in one operation), increasing the accuracy of indexing, correlating or linking multimodality images to the same location along the length of the patient (by coordinating operation of the scanners to a single, controlled movement of the patient) and reducing the labor costs otherwise associated with separate, multimodality scanning operations.

In general, multimodality systems include a series of scanners, each having a different modality, supported by a single housing. Each scanner obtains different information about the patient, which, when combined, provides a better understanding of the patient. More specifically, multimodality cameras typically include a scanner of anatomical structures of the patient (e.g., CT, MRI and Ultrasound cameras) and a scanner of physiologic functions of the patient (e.g., SPECT and PET cameras). The series of scanners forms a relatively long bore, typically longer than the combined head and torso of taller patients and spanning the entire length of shorter patients. The patient is moved at a relatively slow rate through the lengthy multimodality scanning bore, while imaging information is obtained.

The residence time of a patient within the multimodality scanner bore closure typically is in the range of from less than a minute to as much as an hour or more. During much or all of this time, the patient is isolated from operators of the multimodality scanners and cameras, from caregivers who may need to treat the patient, adjust instruments connected to the patient, or perform interventional applications (i.e., image-guided biopsies and the like), and from caregivers who might otherwise attend to the patient, should the patient become upset or ill from ingested radio-pharmaceuticals, and the like. Moreover, the relatively lengthy isolation of the patient within the tight quarters of the bore can cause anxiety, such as claustrophobia, and other discomfort or stress in the patient.

Accordingly, there is a need for a multimodality tomographic imaging system that reduces the isolation of a patient within the scanning bore, provides access by caregivers to the patient and reduces discomfort of the patient.

SUMMARY OF THE INVENTION

The invention comprises a system and method for creating medical images of a subject patient using a plurality of imaging devices, such as tomographic imaging scanners. The system comprises a plurality of imaging devices, each having a bore through which a patient is translated during scanning. The bores of each device are substantially aligned axially with respect to each other. An open area is formed between the imaging devices along the path of the patient, through which a caregiver can attain line-of-sight visual contact with or other access to the patient. During a scanning operation, the scanned portion of a patient is transported through the bore of the first device, past the opening between the devices and into the bore of the second device.

In one aspect of the invention, a fluid control surface is formed by a housing between the plurality of medical imaging devices, to drain fluid falling from the vicinity of the patient outwardly and away from the path of the patient.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION

Figure 1:
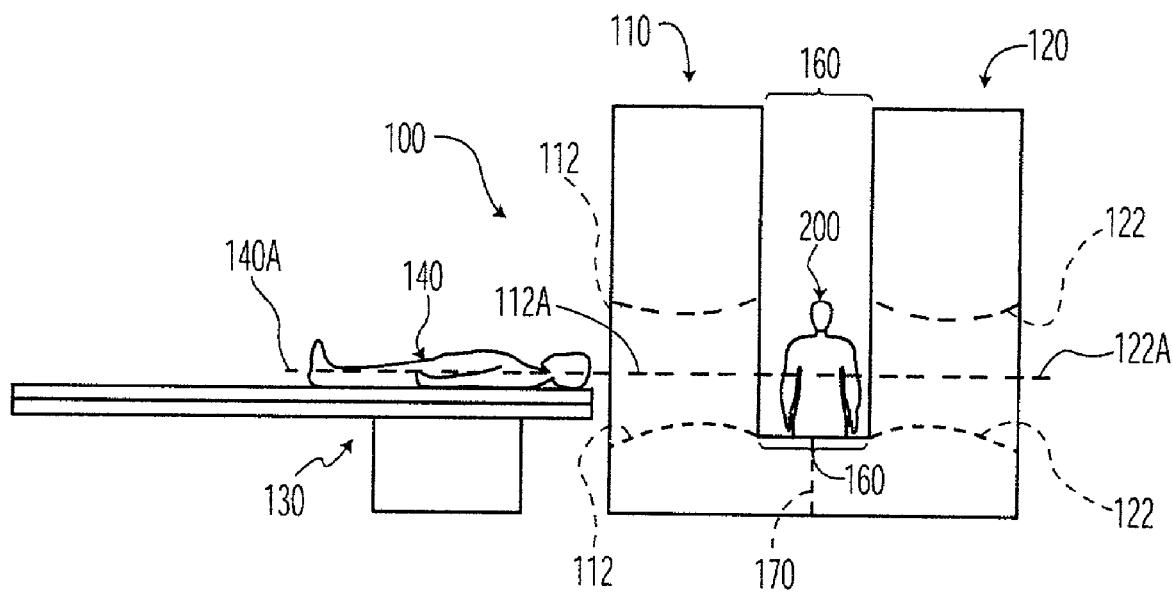
FIG. 1 is a schematic view of the front of a multimodality medical imaging system incorporating the present invention.

Shown in FIG. 1 is a multimodality medical imaging system scanner assembly 100, having first and second imaging devices 110 and 120. In the embodiment shown, each of the imaging devices 110 and 120 comprise at least a scanner having a modality of operation, and may also include associated scanner support structure and associated electronics. Further, in the embodiment shown, each of the imaging devices 110 and 120 includes a scanner opening or bore 112 and 122 (shown by broken lines), respectively, through which a patient table 130 extends and translates a subject patient 140 during a scanning operation. It will be apparent that imaging devices 110 and 120 may alternatively utilize scanners that obtain information about the patient 140 without being configured to form a bore, such as a partial closure, an arrangement of one or more planar detectors and other configurations capable of obtaining patient information. Moreover, it will be apparent that while scanner bores 110 and 120 are preferably circular, other configurations capable of obtaining imaging information may alternatively be utilized.

The patient table 130 serves as a patient support structure that also coordinates movement of the patient 140 with respect to operation of the scanners of the imaging devices 110 and 120, to obtain patient imaging information at one or more desired locations along the length of the patient 140. It will be apparent that a variety of available conventional patient table 130 designs would be suitable for these purposes. It will be apparent that the patient table 130 may be designed or operated to extend the patient 140 past the scanners of the imaging devices 110 and 120 in a variety of methods, such as at a continuous rate, at variable rates, in incremental displacements or a combination of such methods, as may be desired or suitable for the scanning operation to be conducted.

The imaging devices 110 and 120 acquire, through their scanners, information from the patient 140 sufficient to form tomographic images of the patient. Each of the imaging devices 110 and 120 is coupled to one or more conventional tomographic imaging processor(s), utilizing conventional imaging software to form images from information received from the imaging devices 110 and 120.

Preferably, the imaging devices 110 and 120 cooperate to obtain patient information through different modalities, to provide anatomical structure images and physiologic function images of the patient 140. More specifically, imaging device 110 is preferably a CT scanner that utilizes X-rays as the mode of obtaining data from which images depicting the internal structure of the patient 140 are formed. On the other hand, imaging device 120 is preferably a nuclear camera, such as a PET scanner that utilizes positron emissions originating from a radio-pharmaceutical ingested by the patient as the mode of acquiring data from which images depicting primarily metabolic physiological functions within the patient 140 are formed. During operation, the head and torso of the patient 140 are passed through the bores 112 and 122 of the respective imaging devices 110 and 120, and their respective scanners, so that a collection of one or more images are obtained from each scanner.

Figure 2:
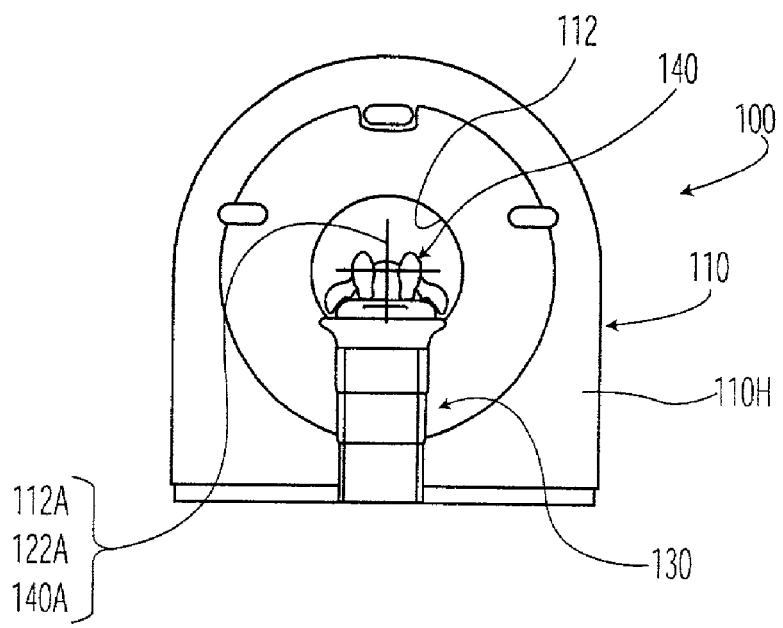
FIG. 2 is a schematic view of the end of the system shown in FIG. 1 at which the patient is inserted into a scanner bore.

Referring now to both FIGS. 1 and 2, the scanner bores 112 and 122 of the imaging devices 110 and 120 are substantially circular, thus surrounding the patient during imaging scanning operations. The axes 112A and 122A of the respective circular openings of each of the bores 112 and 122 are aligned with each other and are preferably aligned with or at least substantially parallel to the path of travel of the patient 140 on the patient table 130. This allows the patient table 130 to translate the patient 140 through the imaging devices 110 and 120 in one substantially continuous pass. Preferably, the center line of the patient 140 is substantially aligned with or at least substantially parallel to the axes 112A and 122A of the detector bores 112 and 122 by adjusting the height of the patient table 130 and the alignment of the table 130 with the bores 112 and 122.

Figure 3:
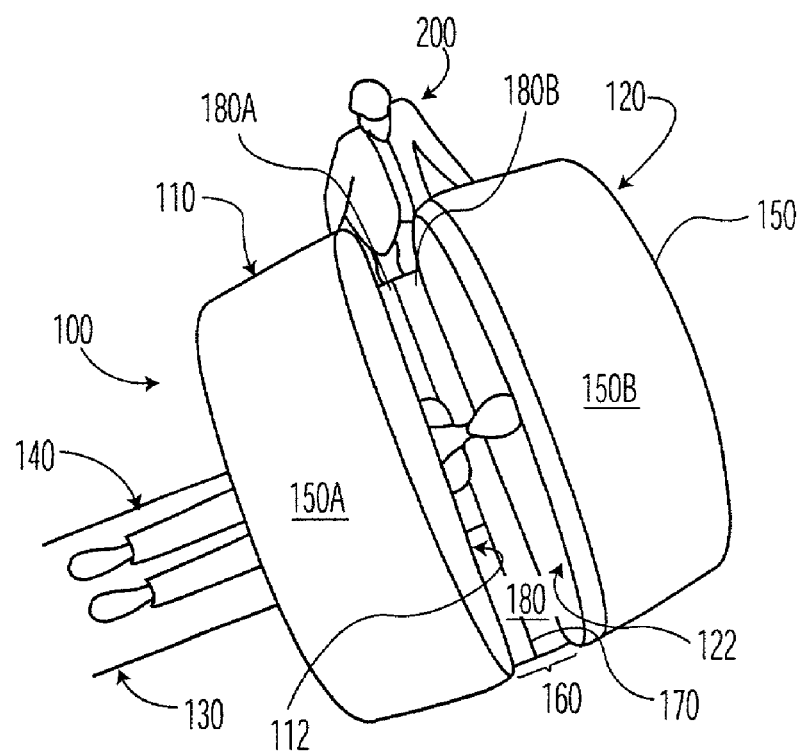
FIG. 3 is a perspective view of the system shown in FIG. 1, taken from the position above the assembly, illustrating in more detail the configuration of the housing, scanners and access area of an embodiment of the invention.
Figure 4:
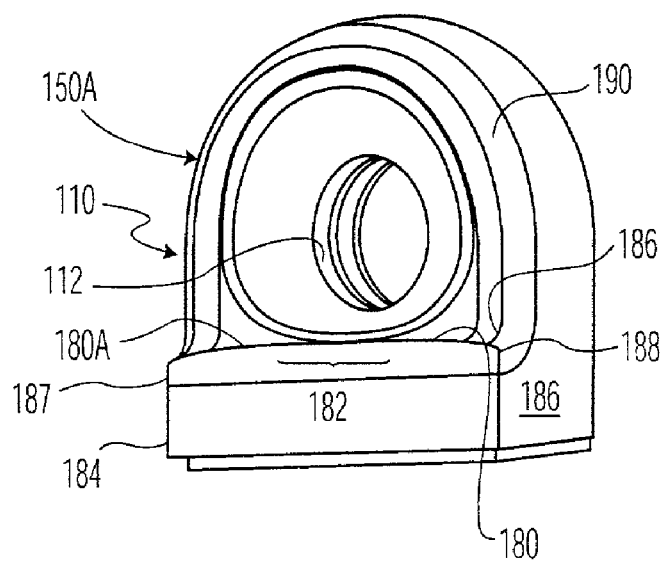
FIG. 4 is a perspective view of a section of the embodiment shown in FIG. 3 illustrating one of two scanners and its associated housing.
Figure 5:
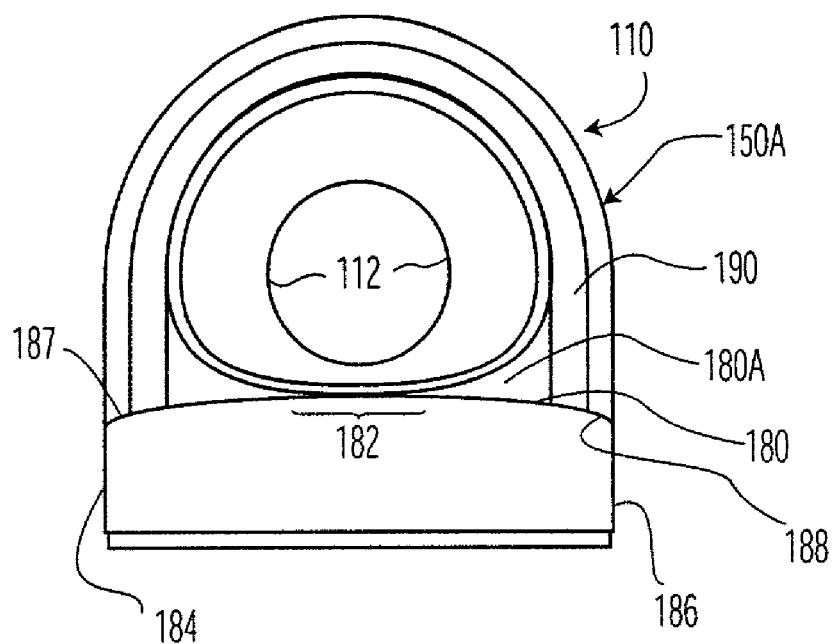
FIG. 5 is a side elevation of the section of the embodiment shown in FIG. 4.
Figure 6:
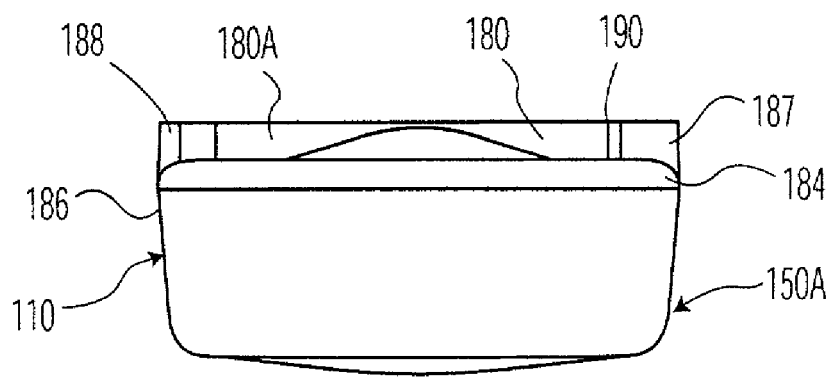
FIG. 6 is a top view of the section of the embodiment shown in FIG. 4.

As is best shown in FIGS. 1, 2 and 3, the imaging devices 110 and 120 are each supported within a housing 150, which is preferably formed from painted sheet metal and is electrically isolated from internal conductors. Alternatively, the housing 150 is formed from fiberglass or other non-conductive material. The housing 150 is preferably formed in a unitary construction, by securing together opposing faces of two portions 150A and 150B of the housing 150. Housing portions 150A and 150B contain and support imaging devices 110 and 120, respectively. The opposing faces of the two housing portions 150A and 150B abut and are secured together along seam line 170, below the level of the bores 112 and 122 of the imaging devices 110 and 120. The housing portions 150A and 150B are secured together by bolts (not shown) extending and tightened between their opposing faces, to facilitate separation of the housing for transport, maintenance and the like. However, it will be apparent that various other securing means could alternatively be used, such as a variety of fasteners, glues, thermal welding and the like. It will further be apparent that the housing 150 could alternatively be constructed in as a single, integral unit.

The housing 150 supports and maintains the bores 112 and 122 of imaging devices 110 and 120 in relatively fixed positions, separated by the width of access area 160. It will be apparent that the fixed positioning and support of the detectors 110 and 120 may be accomplished by the housing 150 acting as the sole support structure or acting in combination with a frame or gantry (not shown) within the housing 150.

The access area 160 formed by the separation of the imaging devices 110 and 120 allows a caregiver 200 to have access to the patient 140 as the patient table 130 translates the patient 140 from the CT scanner 110 to the PET scanner 120 during imaging operations. Such access includes the ability of the caregiver 200 to maintain a direct, line-of-sight contact with the patient and for the patient to see the caregiver 200. In addition, the access area 160 allows the caregiver 200 sufficient room to adjust instruments connected to the patient 140 and to conduct interventional imaging applications, such as inserting needles and adjusting needle alignment mechanisms for image guided biopsies, and the like. The patient access area 160 also allows care to be given to the patient 140 immediately, should the patient become sick due to chemical indicators ingested or for any other reason. Moreover, the access area 160 provides relief to the patient from stress, such as claustrophobia, that may result from residence within the bore 112 of the CT detector 110. The access area 160 allows such access to be had to the patient 140 without disrupting the scanning procedure. While the caregiver 160 is shown to be an individual, it will be apparent that the term "caregiver" includes any means of providing monitoring, diagnostic, treatment, comfort or other care services to the patient 140, such as by use of robotics or other equipment.

The width of access area 160 is preferably approximately 12-18 inches. The access area 160 of the embodiment shown provides an unobstructed, open area of substantially continuous width. The access port extends upwardly, from a location below the patient table 130 and at or below a horizontal plane intersecting the lowest point on the perimeter of the scanners of the imaging devices 110 and 120, through the top of the housing 150. The view afforded a patient 140 lying on her back on the patient table while being moved or translated horizontally between imaging devices 110 and 120 is thus unobstructed in an arc of approximately 180 degrees. It will be apparent that the access area 160 could alternatively be formed on just one side of the housing 150. In another alternative, the access area 160 or could comprise an opening of more limited size, such as a porthole or window through which the patient 140 may be viewed or a caregiver 200 could reach the patient and instruments in the vicinity of the patient.

A multimodality scanning operation begins with the patient 140 being positioned on the patient table 130 outside but adjacent to the bore 112 of the CT scanner of the imaging device 110, as is shown in FIG. 1. The vertical height of the table 130 is adjusted to substantially align the longitudinal axis 140A of the patient 140 substantially with the axes 112A and 122A of the circular scanner bores 112 and 122. The substantially aligned axes 112A and 122A of the scanner bores 112 and 122 combine to form an imaging axis that passes through the imaging planes of the scanners. In the event that the imaging devices 110 and 120 utilize scanners that are not circular, the imaging axis would pass through the imaging areas of the scanners. The patient table 130 then extends and translates the patient horizontally, introducing the patient 140 into the CT scanner bore of the first imaging device 110, as the CT scanner operates using X-rays as a first mode of obtaining information about the anatomical structure of the patient 140.

The patient 140 continues to be translated horizontally through the scanner bore 112 of the first medical imaging device 110 until her head emerges into the access area 160 of the scanner assembly 100, as is shown in FIG. 3. At this point, the patient 140 is provided relief from the confines of the scanner bore 112, may have direct line-of-sight contact with the caregiver 200 and the caregiver 200 may access to the patient 140 for multiple purposes related to the well-being of the patient 140.

As translation of the patient 140 continues, she is introduced into the PET scanner bore 122 of the second imaging device 110, as the PET scanner operates using positron emissions as a second mode of obtaining information about the physiological function of the patient 140. At this point, the patient 140 continues to be translated horizontally through both the CT and PET scanner bores 112 and 122 of the first and second medical imaging devices 110 and 120.

Translation of the patient 140 by the patient table 130 typically will continue until all desired portions of the patient 140 have been scanned by both scanners of the imaging devices 110 and 120. In the process, all scanned portions of the patient 140 will pass through the imaging areas or, in the case of circular scanners such as conventional CT and PET scanners, through the imaging planes of the scanner assembly 100. As this translation of the patient occurs, portions of the patient 140 being scanned are translated through the access area 160, where the caregiver 200 can adjust and manipulate instruments and equipment involved in the imaging or any related interventional application. It will be apparent that the invention is not limited to applications in which both scanners of the first and second imaging devices 110 and 120 are utilized or in which both scanners obtain imaging information about the same portions of the patient 140.

When scanning is complete, the patient is retracted in the opposite horizontal direction by the patient table 130, typically at a faster rate than during the scanning operation, to withdraw the patient 140 from the scanner assembly 100, to the starting position at the beginning of the scanning procedure.

Maintaining the imaging devices 110 and 120 in fixed relation to each other allows images created from the data the scanners separately obtain to be registered correlated, indexed or linked in relation to each other, using information indicating the position of the patient 140 on the patient table 130. More specifically, the patient table 130 is conventional and includes means for detecting the displacement and position of the patient relative to the multimode scanners of the imaging devices 110 and 120. This information can be used in combination with information indicating the fixed distance separating the scanning planes of the imaging devices 110 and 120 to register, correlate, pair or link the images from each of the devices 110 and 120 to a particular location or point on the patient 140. Each tomographic image obtained from imaging device 110 may thus be paired with or indexed to a corresponding tomographic image obtained from detector 120 with reference to substantially the same location along the length of the patient 140.

Referring now to FIGS. 3, 4, 5 and 6, shown is the configuration of the housing portion 150A of the first imaging device 120, forming a portion 180A of a drainage surface 180 for diverting liquids falling from the patient or from other sources within the access area 160. It will be understood that housing portion 150B has a similar drainage surface portion 180B shown in FIG. 3, such that a substantially continuous drainage surface 180 is formed when housing portions 150A and 150B are secured together along seam line 170. The views shown of drainage surface 180A of housing portion 150A thus shows in cross-section the configuration of the drainage surface 180 formed by the housing 150.

The drainage surface 180, 180A has an upwardly arched surface peaking in a centrally located area 182 beneath the bore 112. The surface 180, 180A extends outwardly toward the lateral sides 184 and 186 of the housing portion 150A and downwardly from the central area 182. This forms a crowned surface, which causes liquids (e.g., medications, vomit and the like) falling to the drainage surface 180, 180A to flow outwardly, away from the patient. The drainage surface 180, 180A is provides sufficient clearance beneath the bores 112 and 122 and the patient table 130 to avoid interference with vertical alignment and horizontal translation of the patient 140. Rounded lateral shoulders 187 and 188 form gradual transitions from the drainage surface 180, 180A to the lateral sides 184 and 186, respectively of the housing 150, 150A, to avoid harm to caregivers 200 and others accessing the patient 140 through the access area 160. A curved surface 189 transitions between the drainage surface 180, 180A and the vertical surface 190 of the housing portion 150A surrounding the bore 112, to facilitate cleaning such surfaces. Shoulders and surfaces similar to shoulders 187 and surfaces 189 are incorporated in housing portion 150B, to provide a substantially symmetrical configuration.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

The invention claimed is:

1. A medical imaging apparatus, comprising:
a CT imaging device for obtaining one or more tomographic images of a subject patient, the CT imaging device having a first housing which defines a bore through which the patient axially translates during formation of one or more images by the device;
a nuclear camera imaging device for obtaining one or more tomographic images of the subject patient, nuclear camera imaging device having a second housing which defines a bore through which a patient axially translates during formation of the images by the device, which first and second housings are selectably securable in a fixed abutting position to one another during the formation of one or more images of the subject patient, in which fixed position the bore of each device is substantially aligned axially with the bore of the other; and
when the first and second housings are secured in a fixed abutting position to one another, the bores of the CT and nuclear camera imaging devices are spaced apart by a distance sufficient to allow direct access by a caregiver to a portion of the subject patient which is positioned between the first and second bores, the spacing between the bores is free of obstructions in a region above the subject patient.

2. An imaging apparatus having an imaging axis, comprising:
separatable first and second imaging devices for obtaining one or more images of a patient, wherein the patient is substantially aligned with the imaging axis;
a first housing which houses the first imaging device and defines a first bore; and
a second housing which houses the second imaging device and defines a second bore;
projecting engageable securement structures which extend from at least one of the first housing and the second housing to fixedly attach the first and second imaging devices in positions abutting each other and fixed relative to the imaging axis; and
an opening formed between the first and second bores when the first and second housings are abutting through which opening a caregiver can have line-of-sight visual contact with the patient that is aligned with the imaging axis and extends between the first and second imaging devices.

3. A medical imaging apparatus, comprising:
a first tomographic medical imaging device having an opening for receipt of a subject patient;
a second tomographic medical imaging device having an opening for receipt of the subject patient;
a patient support structure extending through the openings of the first and second imaging devices during the formation of one or more images by at least one of the imaging devices;
an imaging device support structure securing the first and second imaging devices in a fixed abutting relationship with the openings of the first and second imaging devices in alignment with an imaging axis during the formation of one or more tomographic images, by at least one of the imaging devices, of the subject patient;
which imaging device support structure forms a patient access area between the first and second imaging devices through which a caregiver can directly observe the subject patient between the openings of the first and second imaging devices; and
an arcuate drainage surface which is formed as a portion of a housing of either the first or second medical imaging device and positioned between the first and second imaging devices underneath the patient support structure when the imaging devices are secured together.

4. The medical imaging apparatus of claim 3, wherein the patient access area allows direct tactile contact between a caregiver and the subject patient.

5. The medical imaging apparatus of claim 3, wherein the patient access area allows a caregiver to perform one or more interventional applications on the subject patient between the first and second imaging devices.

6. The medical imaging apparatus of claim 5, wherein the patient access area allows a caregiver to perform at least a portion of a biopsy procedure on the subject patient.

7. The medical imaging apparatus of claim 3, wherein the first imaging device comprises one of a group consisting of CT, MRI, X-Ray, and Ultrasound devices.

8. The medical imaging apparatus of claim 7, wherein the second imaging device comprises one of a group consisting of SPECT and PET devices.

9. The medical imaging apparatus of claim 3, wherein the axes of openings of the first and second imaging devices are substantially aligned.

10. A medical imaging apparatus, including:
a first medical imaging device having a housing which defines a first bore;
a second medical imaging device having a housing which defines a second bore;
a patient support structure which supports a subject patient during imaging; and
a support structure for securing the first and second bores in a fixed abutting relationship, which support structure forms a patient access area between the first and second imaging devices, a part of the support structure defining a fluid control surface formed by the housing of either the first or second medical imaging device and positioned beneath the patient support structure and between the first and second imaging devices for directing liquids falling onto the surface from the vicinity of the patient support structure away from the subject patient.

11. A medical imaging apparatus, comprising:
a housing having a first scanner and a second scanner, each scanner having a bore for obtaining tomographic imaging information from at least a portion of a patient, which housing positions each of the first and second scanner bores in fixed positions apart from the other during scanning operations and forms a patient access area between the first and second scanners bores to allow direct access by a caregiver to the patient extending through the first scanner bore and at least partially positioned between the first and second scanners; and a substantially continuous arcuate drainage surface which is formed from a portion of said housing in an axial direction, which arcuate drainage surface has a peak located underneath the patient and extends outwardly and downwardly from the peak and toward lateral sides of the housing.

12. The medical imaging apparatus of claim 11, wherein the bores of the first and second scanners have axes that are substantially aligned.

13. The medical imaging apparatus of claim 11, further comprising a patient support means for supporting and positioning first and second portions of a patient simultaneously within the bores of the first and second scanners, respectively, and for supporting and positioning a third portion of the patient between the bores and accessible to a caregiver through the patient access area.

14. The medical imaging apparatus of claim 11, wherein the first and second scanners are adapted to operate in different modalities with respect to each other.

15. The medical imaging apparatus of claim 14, wherein one of the first and second scanners is adapted to obtain imaging information representing anatomical structures of the patient.

16. The medical imaging apparatus of claim 15, wherein one of the first and second scanners is adapted to obtain imaging information representing physiologic functions of the patient.

17. A medical imaging method, comprising:

providing a housing having a first scanner and a second scanner, each scanner having a bore for obtaining tomographic imaging information from at least a portion of a patient;

positioning each of the first and second scanner bores in fixed positions apart from the other during scanning operations;

forming a patient access area in said housing between the first and second scanners bores to allow direct access by a caregiver to a patient extending through the first scanner bore and at least partially positioned between the first and second scanners to allow direct access to the patient by a caregiver through the patient access area formed between the first and second scanners; and draining fluids from a lower end of the patient access area defined by the housing with an arced surface underneath the patient.

18. The medical imaging method of claim 17, further comprising operating the first and second scanners in different modalities with respect to each other to obtain imaging information from the patient.

19. The medical imaging method of claim 18, further comprising operating one of the first and second scanners in a modality obtaining imaging information representing anatomical structures of the patient.

20. The medical imaging method of claim 19, further comprising operating one of the first and second scanners in a modality obtaining imaging information representing physiologic functions of the patient.

21. A medical imaging apparatus, comprising:

a first scanning device for obtaining imaging information from a patient when the patient is disposed in a scanning position;

a housing which houses the first scanning device, the housing defining a drainage surface disposed below at least a portion of a patient support surface, when the patient is in the scanning position, which drainage surface slopes downwardly and away from the patient to drain fluids falling to the surface from the vicinity of the patient, when the patient is in the scanning position.

22. The medical imaging apparatus of claim 21, wherein the drainage surface extends outwardly and downwardly from opposite sides of the patient, when the patient is in the scanning position.

23. The medical imaging apparatus of claim 22, wherein the drainage surface comprises an upwardly arced surface immediately below a patient, when the patient is in the scanning position.

24. The medical imaging apparatus of claim 21, further comprising:

a second scanning device; and wherein the drainage surface extends between and separates the first and second scanning devices to form an access area for a caregiver to access the patient disposed in the scanning position.

25. The medical imaging apparatus of claim 24, further comprising:

a housing supporting the first and second scanning devices and forming at least a portion of the drainage surface area between the first and second scanning devices.

26. The medical imaging apparatus of claim 25, wherein the drainage surface extends outwardly and downwardly from opposite sides of the patient, when the patient is in the scanning position.

27. The medical imaging apparatus of claim 26, wherein the drainage surface comprises:

an upwardly arced surface immediately below a patient, when the patient is in the scanning position.

28. A medical imaging apparatus, comprising:

a first imaging device for obtaining one or more anatomical tomographic images of a subject patient, the first imaging device having a first housing which defines a first imaging region therein; and a second imaging device for obtaining one or more functional tomographic images of the subject patient, the second imaging device having a second housing which defines a second imaging region therein;

wherein the first and second housings are selectably securable in a fixed abutting position to one another; and when the first and second housings are secured in a fixed abutting position to one another, the first and second imaging regions are spaced apart by a distance sufficient to allow access to the subject patient.

29. The medical imaging apparatus for claim 28 further comprising a fluid drainage surface defined as a portion of the first or second housing.

* * * * *